United States Patent

Soled et al.

[11] Patent Number: 5,866,739
[45] Date of Patent: Feb. 2, 1999

[54] HETEROPOLY SALTS OR ACID SALTS DEPOSITED IN THE INTERIOR OF POROUS SUPPORTS

[75] Inventors: Stuart Leon Soled, Pittstown, N.J.; Jose Augusto da Costa Paes, Sao Paulo, Brazil; Antonio Gutierrez, Mercerville, N.J.; Sabato Miseo, Pittstown, N.J.; William E. Gates, Port Murray, N.J.; Kenneth L. Riley, Baton Rouge, La.

[73] Assignee: Exxon Research and Engineering Company, Florham Park, N.J.

[21] Appl. No.: 902,047

[22] Filed: Jul. 29, 1997

Related U.S. Application Data

[60] Continuation of Ser. No. 488,665, Jun. 8, 1995, abandoned, which is a division of Ser. No. 336,364, Nov. 8, 1994, abandoned, which is a continuation-in-part of Ser. No. 156,178, Nov. 15, 1993, abandoned.

[51] Int. Cl.$^6$ ........................................................ C07C 2/70
[52] U.S. Cl. ........................................... 585/467; 585/466
[58] Field of Search .................................... 585/467, 468, 585/466

[56] References Cited

U.S. PATENT DOCUMENTS

| | | |
|---|---|---|
| 3,346,657 | 10/1967 | Henke et al. .......................... 260/671 |
| 4,565,801 | 1/1986 | Shimizu et al. . |
| 4,612,301 | 9/1986 | Currie et al. . |
| 4,687,875 | 8/1987 | Currie et al. . |
| 4,757,044 | 7/1988 | Cooper et al. . |
| 5,177,301 | 1/1993 | Knifton . |
| 5,189,201 | 2/1993 | Sano et al. . |
| 5,254,766 | 10/1993 | Fujita et al. . |
| 5,324,881 | 6/1994 | Kresge et al. . |
| 5,334,775 | 8/1994 | Gutierrez et al. ....................... 568/791 |
| 5,366,945 | 11/1994 | Kresge et al. .......................... 502/60 |

FOREIGN PATENT DOCUMENTS

| | | |
|---|---|---|
| 57-046925 | 3/1982 | Japan . |
| 05009135 | 1/1993 | Japan . |

*Primary Examiner*—Bekir L. Yildirim
*Attorney, Agent, or Firm*—Estelle C. Bakun

[57] ABSTRACT

The present invention relates to a catalyst composition, its methods of preparation and its use in aromatic alkylation processes. The composition comprises a heteropoly compound selected from the group consisting of heteropoly salts and heteropolyacid salts deposited in the interior of a porous support selected from the group consisting of silica, titania, and zirconia, wherein said salt of said heteropoly salt and said heteropolyacid salt is selected from the group consisting of ammonium, cesium, potassium, and rubidium salts and mixtures thereof, and wherein said heteropoly salt and said heteropolyacid salt are formed with a heteropolyacid selected from the group consisting of 12-tungstophosphoric, 12-tungstosilicic, 12-molybdophosphoric, and 12-molybdosilicic acid.

2 Claims, 6 Drawing Sheets

FIGURE 3, VIEW A

FIGURE 3, VIEW B

FIGURE 3, VIEW C

FIGURE 3, VIEW D

HETEROPOLY SALTS OR ACID SALTS DEPOSITED IN THE INTERIOR OF POROUS SUPPORTS

CROSS REFERENCE TO RELATED APPLICATION

This is a continuation of application Ser. No. 488,665, filed Jun. 8, 1995 now abandoned, which is a division of Ser. No. 08/336,364, filed Nov. 8, 1994, now abandoned, which is a continuation in part of Ser. No. 08/156,178, filed Nov. 15, 1993, now abandoned.

FIELD OF THE INVENTION

Various catalysts have been used to alkylate phenols with olefins. Traditionally, such alkylation reactions were carried out at atmospheric pressure with the reactants and catalyst in the liquid phase, referred to as "homogeneous catalysis", utilizing catalysts such as sulfuric acid, boron trifluoride, and aluminum chloride. Alkylation of phenols with olefins of up to 500,000 number average molecular weight have been disclosed, such as in U.S. Pat. No. 4,735,582, and EP Publication 440,507 A2. The drawback of homogeneous catalysis, of course, is the difficulty and expense in removing the catalyst from the liquid product. In addition, the toxic and corrosive nature of the strong acid catalysts mentioned above presents environmental and operational problems.

12-tungstophosphoric acid ($H_3PW_{12}O_{40}$; HPW) has been shown to be an effective catalyst in aromatic alkylations, capable for example of alkylating phenol with olefinic polymers to produce important alkyl phenol intermediates. HPW is very soluble in water (approximately 2 gm HPW/gm $H_2O$ at room temperature) and in other polar solvents. Even supported HPW will solubilize. Although phenol is substantially less polar than water, it will solubilize some HPW (12-tungstophosphoric acid) at temperatures (130°–170° C.) used to alkylate phenol and olefins. This limits the utility of the acid because it is consumed in a short time and contaminates the product. HPW has an approximate solubility of p0.3–1.0% in phenol at 170° C. The cesium and ammonium salts or acid salts of HPW are negligibly soluble in water at room temperature and phenol at reaction temperatures. However, these salts, when prepared by techniques known in the prior art, form submicron (100Å) water-insoluble particles which produce large pressure drops when used in fixed bed applications. Furthermore by virtue of their insolubility, they cannot be deposited in the interior of porous supports by simply dissolving them in solution and impregnating; the classical prior art technique. It is readily apparent to those skilled in the art that, if the insoluble precipitates are produced outside of the support particle, they will form only a coating of the salt on the outer surface of support particles, especially large extrudates since the particle size of the precipitate particle exceeds that of the pore diameter of the support material. The technique suffers from problems associated with attrition and adherence of the outer coating. What is needed in the art is a way of supporting the heteropoly salts or acid-salts deposited in the interior of porous large particle carriers.

SUMMARY OF THE INVENTION

The present invention relates to a catalyst composition, its methods of preparation and its use in aromatic alkylation processes. The present invention relates to a novel catalyst composition comprising a heteropoly compound selected from the group consisting of heteropoly salts and heteropolyacid salts deposited in the interior of a porous support selected from the group consisting of silica, titania, and zirconia, wherein said salt of said heteropoly salt and said heteropolyacid salt is selected from the group consisting of ammonium, cesium, potassium, and rubidium salts and mixtures thereof, and wherein said heteropoly salt and said heteropolyacid salt are formed with a heteropolyacid selected from the group consisting of 12-tungstophosphoric, 12-tungstosilicic, 12-molybdophosphoric, and 12-molybdosilicic acid.

The invention is further directed to the method of preparing catalyst compositions comprising the steps of:

(a) impregnating a soluble precursor into a support selected from the group consisting of silica, titania, and zirconia, wherein said soluble precursor is selected from the group consisting of a heteropolyacid, the 100°–250° C. hydrothermal reaction product of ammonium metatungstate with ammonium phosphate dibasic, the 150° C. hydrothermal reaction product of ammonium molybate with ammonium phosphate dibasic, a solution of a mixture of urea and a heteropolyacid, a water soluble cesium salt, a water soluble Rb salt, and a water soluble K salt, wherein said heteropolyacids are selected from the group consisting of 12-tungstophosphoric acid, 12-tungstosilicic acid, 12-molybdophosphoric acid and 12-molybdosilicic acid;

(b) drying said silica support having said soluble precursor impregnated therein at about 90° to about 130° C.;

(c) thermally treating said dried support at about 200° to about 350° C. wherein when said soluble precursor is a heteropolyacid, a source of ammonia gas is passed over the dried support at a temperature of about 100°–150° C. followed by thermal treatment;

(d) impregnating said thermally treated support with a heteropolyacid when said soluble precursor selected from the group consisting of a water soluble cesium, rubidium and potassium salt followed by drying at about 90° to about 150° C. and calcination at about 200° to about 350° C. and wherein said heteropolyacid is selected from the group of heteropolyacids of step (a) resulting in the deposition of the salt or acid-salt in the interior of the porous support.

DETAILED DESCRIPTION OF THE INVENTION

Heteropoly acids form by condensation of two or more oxyacids, e.g., phosphoric or silicic acid with tungstic acid, and contain large polyoxometallate anions with interstitial hydrated protons and variable levels of water of hydration. The heteropoly acids are soluble in water or polar oxygenated hydrocarbons, such as alcohols or ethers. The particular heteropoly acids of the present catalysts contain anions adopting the well known Keggin structure and are represented by formulas: $H_3PW_{12}O_{40} \cdot 6H_2O$ (phosphotungstic acid also referred to as 12-tungstophosphoric acid. $H_4SiW_{12}O_{40} \cdot 6H_2O$ (12-tungstosilicic acid or silicotungstic acid), $H_3PMo_{12}O_{40} \cdot 6H_2O$ (12-molybdophosphoric acid), and $H_4SiMo_{12}O_{40} \cdot 6H_2O$ (12-molybdosilicic acid). They contain e.g., a central tetrahedral $PO_4$ or $SiO_4$ group connected to 12 surrounding $WO_6$ octahedra and can be considered e.g., the condensation product of phosphoric acid with tungstic acid or phosphoric acid with silicic acid, etc.

Although such water soluble heteropoly acids can be readily deposited on supports by impregnation techniques, their Cs, $NH_4$, K and Rb salt counterparts are water insoluble and current means for impregnating them onto supports or into the interior of the porous supports are unknown. The current invention describes a way of preparing support catalyst wherein such insoluble salts or acid salts are deposited in the interior of porous supports.

The instant invention encompasses both heteropoly salts and heteropolyacid salts. During the preparation of the catalysts, a heteropolyacid is employed and in situ formation of the salt or acid salt occurs. In the instant invention at least 1.5 protons of the acid will be exchanged and up to three protons may be exchanged with the designated cations for heteropoly acids containing 3 protons. If less than three protons are exchanged the acid salt will be formed, if all (3) of the protons are exchanged, the salt will be formed. For cesium catalysts, exchange of 2.5 protons is preferred. For heteropolyacids containing 4 protons, at least 2.5 protons of the acid will be exchanged and up to 4 protons may be exchanged. If all 4 are exchanged, the salt results. If 2.5 to 3.9 protons are exchanged, the acid salt results.

The preferred support utilized in the present invention is a high surface area porous silica support. Such supports are commercially available or may be prepared by well known techniques. Preferably the support will be thermally treated prior to use. For example, the silica may be calcined at about 500° C. The silica support utilized will be one preferably useable for fixed-bed reactions. Therefore, it is preferable that the silica be present in the form of extrudates although other forms are possible. Additionally the instant catalysts can be used in fluidized bed systems. Hence, the particle size of the support can range from 0.1 mm powder to $\frac{1}{8}'' \times \frac{1}{2}''$ extrudates and 1 to 3 mm diameter spheres. Other supports utilizable are supports that will allow the heteropoly salt or acid salt to retain its structure as micro crystallites within the pore structure of the porous support, e.g., $ZrO_2$ and $TiO_2$.

The salts of the invention have the general formula $H_{3-x}M_xPQ_{12}O_{40}$ where $x=3$, $M=K$, Cs, Rb and $H_{4-x}M_xSiQ_{12}O_{40}$ where $x=4$, $M=Cs$, K, Rb, $NH_4$. Q=tungsten or molybdenum in each of the above formulas. The acid salts have the same general formulas except that $x=1.5$ to 2.9 inclusive and 2.5 to 3.9 inclusive, respectively.

As used in the instant invention, the heteropoly acids are converted to their corresponding salts or acid salts. Suitable salts include the salts of ammonium, cesium, potassium, rubidium and mixtures thereof with ammonium and cesium being preferred. The salt cations substitute for from 1.5 to 2.9 of the protons of the heteropoly acid in a heteropoly acid containing three hydrogens. For example:

$$H_3PW_{12}O_{40} \cdot 6H_2O = (H_5O_2)^+_{3}PW_{12}O_{40}$$

can be exchanged with ammonium to the salt $$(NH_4)_3PW_{12}O_{40}$$

or acid salt. Representative of two acid salts are $$(NH_4)_{2.5}H_{0.5}PW_{12}O_{40} \text{ or } (NH_4)_2HPW_{12}O_{40}$$

The amount of heteropoly acid salt or heteropolysalt incorporated onto the silica support will range from 2 to 60 wt %, preferably 10 to 40 wt %.

The catalysts of the present invention are prepared by impregnating a water soluble precursor into the interior of a porous support such as porous silica and then converting the precursor in situ into the desired heteropoly acid salt or heteropoly salt. The soluble precursors include a heteropolyacid, a mixture of urea and a heteropolyacid, a water soluble cesium, rubidium or potassium salt, and the 100° to 250° C. hydrothermal reaction product of ammonium metatungstate or ammonium molybdate with ammonium phosphate dibasic. The impregnated supports are then dried at 90° to about 130° followed by calcination at about 200° to about 350° C. When the soluble precursor is a heteropolyacid, the impregnated support is contacted with ammonia during the drying step. In the case of a soluble cesium, rubidium or potassium salt as the soluble precursor, following drying and calcination the impregnated support is reimpregnated with a heteropolyacid and the drying and calcination steps are repeated. Thus, the desired heteropoly salt or heteropolyacid salt is formed in situ in the interior of the porous support.

Figure 3:
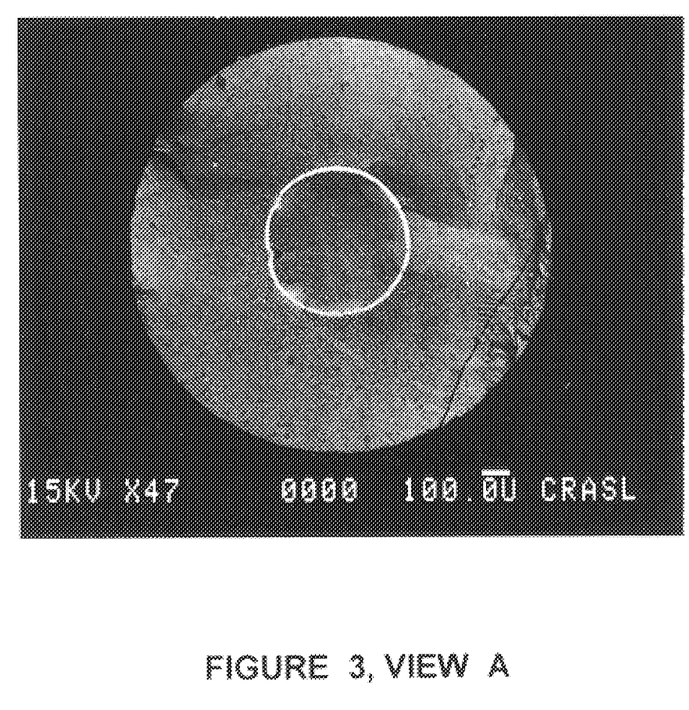
FIG. 3, views A, B, C, and D, shows that the cesium catalysts of the instant invention form what is referred to in the art as an egg white catalyst. The pictures are of a cross-sectional view of a cesium acid salt catalyst prepared in accordance with the instant invention.

In the case of cesium containing catalysts, the cesium acid salt is present in a zone remote from both the center and the external surface of the support, which can be described as a catalytically active ring of about 10 to about 20 microns thick present within the interior of the support. Such a catalyst is referred to in the art as an egg white catalyst (see "Theory of Preparation of Supported Catalysts," Neimark, et al., Ind. Eng. Chem. Prod. Res. Dev. 1981, 20, 439–450). Refer to FIG. 3.

Specifically, incorporation of the ammonium heteropoly acid salt onto a silica support can be achieved in the following ways. The desired heteropoly acid may first be incorporated onto the silica support by well known techniques. The supported heteropoly acid is then treated with a gaseous mixture of ammonium in nitrogen for a time and at a space velocity sufficient to titrate substantially all of the protons of the heteropoly acid with $NH_3$. For example a 5% $NH_3/N_2$ gaseous mixture treatment at 150° C. can be used. Such treatment criteria are readily determinable.

Secondly, it has been found that a soluble precursor can be formed by hydrothermally reacting ammonium metatungstate and ammonium phosphate dibasic in a 12W/1P (12 tungsten/1 phosphorus) molar ratio. The materials are dissolved in water and heated in an autoclave to 150° C. overnight followed by impregnation onto silica. Subsequent drying and calcination then form the heteropolysalt desired.

Alternatively, urea may be added to HPW (12-tungstophosphoric acid) in a mole ratio of urea to HPW of 0.5 to ⅔ and impregnated onto silica, followed by calcination at 400° C.

Cesium catalysts may be prepared via sequential impregnation techniques and in situ reaction. Such techniques involve first reacting soluble cesium salt onto, e.g., a silica support, drying and calcining, followed by impregnation with the soluble heteropoly acid, drying and calcining. Such materials appear to be the result of an in situ reaction between the cesium salt and the acid on the support. Suitable cesium salts are any water soluble cesium salts such as cesium carbonate and cesium nitrate. Drying is conducted between about 90° and 150° C. and calcining between about 200° and 350° C.

The invention is further directed to the use of the instant catalysts in an aromatic alkylation process. The aromatic starting material for aromatic alkylation can be benzene, phenol, toluene or a combination of the three. Olefinic starting materials include olefins of $C_2$ up to and including olefins having a molecular weight of 5000. For example, on the very low end, olefins such as ethylene or propylene would be suitable, polymeric olefins could be used as well. Generally, the heteropoly catalyst will be charged to provide at least about 0.001, preferably from 0.1 to 0.9, more preferably from 0.05 to 0.4, moles of catalyst per mole of polymer alkylating agent charged to the alkylation reaction zone. Use of greater than 1 mole of the inorganic catalyst per mole of polymer alkylating agent is not generally required.

The temperature for alkylation can also vary widely, and will typically range from 20° to 250° C., preferably from 30° to 200° C., more preferably from 100° to 180° C.

For phenol alkylation with a polymeric olefin, the reaction temperature will also affect the ratio of para-substituted to ortho-substituted reaction product. Reaction temperatures about 130° C. will favor nearly equal amounts (i.e., racemic) of ortho- and para-substituted alkylated aromatic, anywhere from about 40 to 60% by weight of one to 60 to 40% by weight of the other. Very little disubstituted alkylated aromatic has been found at any of the temperatures tested. Reaction temperatures below 130° C. yield increasing proportions of para-substituted product. The actual temperature at which the transition occurs depends upon the molecular weight of the alkylating agent.

For industrial purposes a preferred temperature range is from about 150° C. to about 250° C. At these temperatures, the polymer alkylating agent is an easy to handle liquid, the reaction occurs rapidly, and the product mixture is approximately racemic.

The alkylation reaction time can vary and will generally be from 0.5 to 5 hours, although longer or shorter times can also be employed. The alkylation process can be practiced in a batchwise, continuous or semicontinuous manner.

The reaction may be carried out with or without a solvent. The solvents may be polar or non-polar with the proviso that they are not to be protic. Non-polar solvents are preferred since solvents of high enough polarity, even if non-protic, may cause partial or complete dissolution of the catalyst. Hence, preferred solvents include the aliphatic hydrocarbons, aromatic hydrocarbons, ethers, halogenated hydrocarbons, etc.

Preferred solvents are those sufficiently less volatile than water, under the reaction conditions utilized, so as to allow water to be driven out of the reaction mixture with minimal loss of solvent. Such solvents include the hydroxyaromatic reactants themselves as well as the dichlorobenzenes (ortho, meta, and para), heptane, decane, and the like.

For mass production it is preferred that a continuous process be utilized. This involves continuously introducing reactants and solvents into a reaction zone and continuously drawing off the products of the reaction. Hence, it is advantageous to use extrudates as is possible with the present invention. Although the unsupported $NH_4$ and Cs acid salts are known in the art to work as catalysts, they could not be prepared as extrudates as the present acid salts and salts deposited in the interior of porous support extrudates can.

Means for either retaining the catalyst in the reaction zone are preferred, otherwise means for separating the catalyst from the product effluent and recycling it back to the reaction zone are required.

EXAMPLES

Example 1

8.1%$(NH_4)_{3-x}H_xPW_{12}O_4/SiO_2$ powder (Davison 62), wherein x is equal to or less than 0.5.

Figure 1:
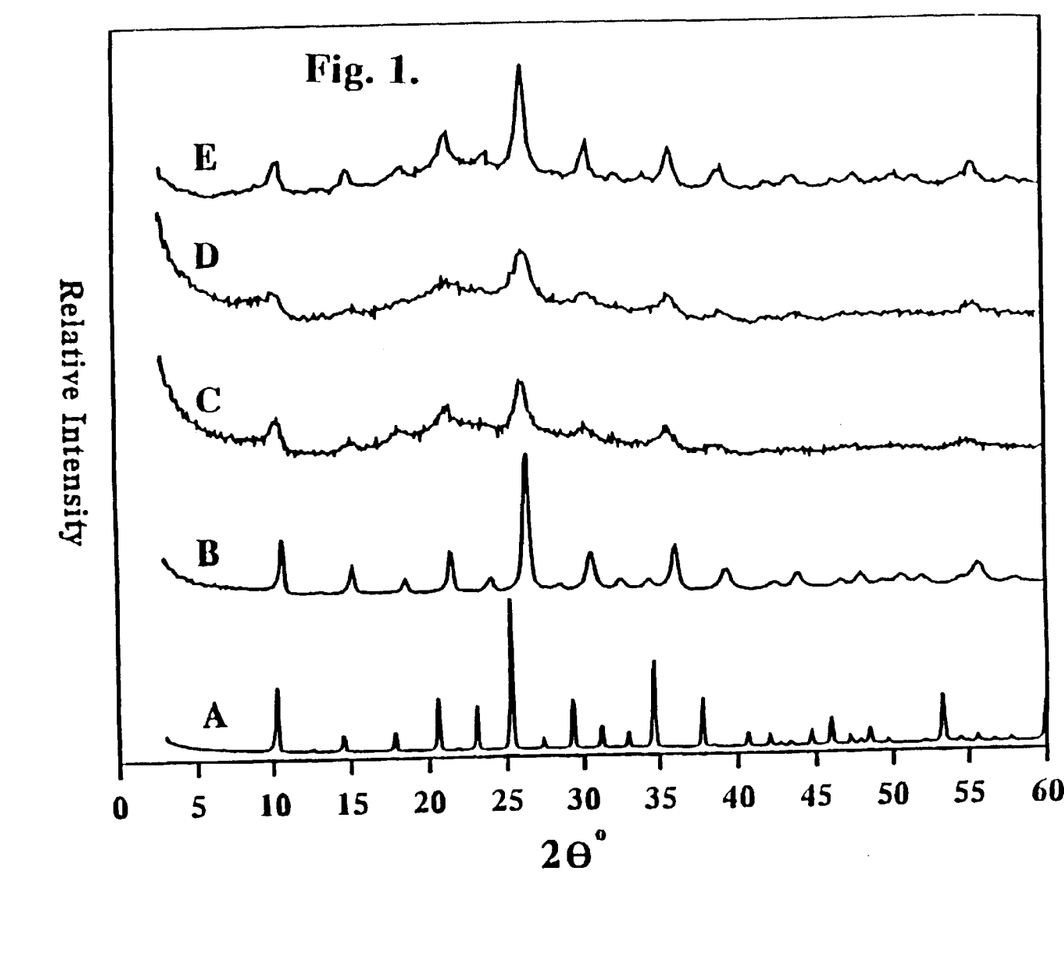
FIG. 1 shows the x-ray diffraction spectra of bulk and silica supported ammonium salts of 12-tungstophosphoric acid. The x axis is two theta (degrees) and the y axis is relative intensity. Lines A, B, C, D, and E depict bulk 12-tungstophosphoric acid, bulk $(NH_4)_{3-x}H_xPW12O_{40}$, 24.3% $(NH_4)_{3-x}H_xPW_{12}/SiO_2$ prepared via a reaction of $H_3PW_{12}O_{40}.6H_2O$ and $NH_3$ gas, 24.3% $(NH_4)_{3-x}H_xPW_{12}/SiO_2$ prepared via an autoclave preparation, and 40% $(NH_4)_{3-x}H_xPW_{12}/SiO_2$ prepared via impregnation and calcination of an urea and 12-tungstophosphoric acid solution, respectively, wherein x is equal to or less than 0.5. The silica in all of the preparations has a surface area of 270 $m^2/g$.

Catalyst Preparation: autoclave preparation of supported ammonium salt: 45.6 grams of ammonium metatungstate (92.2% $WO_3$) was dissolved along with 2.0 grams of ammonium phosphate dibasic in 120 cc of water. The solution was placed in a 300 cc autoclave, stirred, and the temperature was raised to 150° C over a period of 5 hours and held at this temperature for 2.5 hours. After the autoclave was cooled, a clear solution weighing 160 gm was removed. 12.8 grams of this solution was taken and water was added to give a total volume of 50 cc. This solution was impregnated to the point of incipient wetness onto a silica powder (Davison 62) precalcined at 600° C. overnight and possessing a surface area of 270 $m^2/g$. The sample was then dried at 120° C. and calcined at 300° C. for 3 hours. A second catalyst was prepared corresponding to 24.3%$(NH_4)_{3-x}H_xPW_{12}O_{40}/SiO_2$ by impregnating 40 grams of Davison 62 silica with 46.4 grams of the autoclave liquid to which water is added to give a total volume of 50 cc. This catalyst was also dried at 120° C. overnight and calcined at 300° C. for three hours. FIG. 1 shows the X-ray diffraction spectra of the 24.3% $(NH_4)_{3-x}H_xPW_{12}O_{40}/SiO_2$ catalysts compared to the parent 12-tungstophosphoric acid and the conventionally prepared bulk $(NH_4)_{3-x}H_xPW_{12}O_{40}$ salt and shows that the impregnated autoclave reaction product produces a supported ammonium salt on drying and calcination.

Example 2

Silica supported cesium acid salt: 30% $CS_{2.5}H_{0.5}PW_{12}O_{40}/SiO_2$ by sequential impregnation (Davison 62 silica powder).

Figure 2:
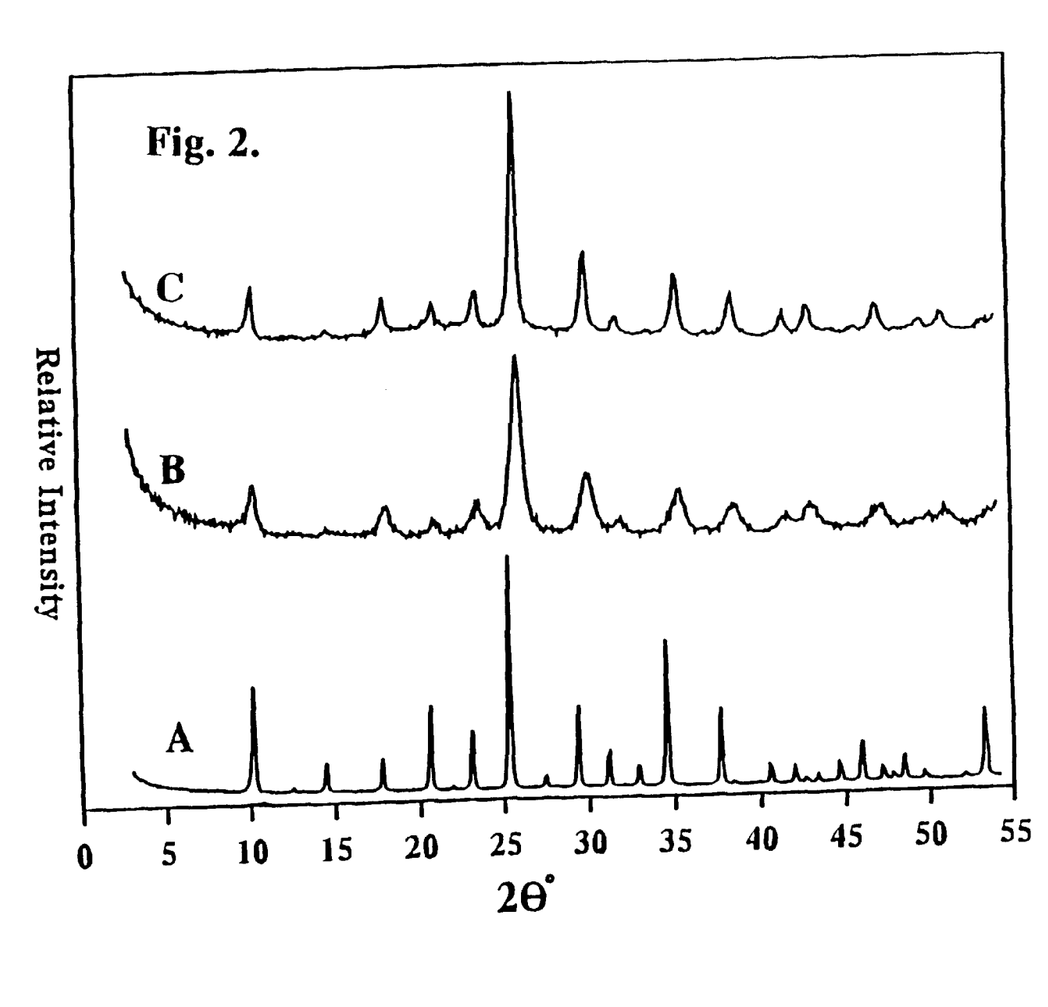
FIG. 2 shows the x-ray diffraction spectra of bulk and silica supported cesium acid salts of 12-tungstophosphoric acid. The x axis is two theta (degrees) and the y axis relative intensity. Lines A, B, and C depict bulk 12-tungstophosphoric acid, bulk $Cs_{2.5}H_{0.5}PW_{12}O_{40}$ and 40% $Cs_{2.5}H_{0.5}PW_{12}O_{40}/SiO_2$ prepared by sequential impregnation and in situ reaction.

Catalyst Preparation: 40 grams of a Davison 62 powder silica meshed to 60/80 size and precalcined at 600° C. overnight was selected. 2.16grams of cesium carbonate was dissolved in 55 cc $H_2O$ and this solution was impregnated to the point of incipient wetness onto the silica powder. The sample was then dried at 120° C., and calcined at 300° C. for 3 hours. A solution of 15.96 grams of $H_3PW_{12}O_{40}.6H_2O$ which was prepared from a commercial supply (Allan Chemicals) by drying at 120° C. was then dissolved in 55 cc of $H_2O$ and impregnated by incipient wetness onto Cs-impregnated silica, dried overnight at 120° C. and calcined at 300° C. for three hours. To check that all the 12-tungstophosphoric acid reacted to form the insoluble Cs-acid salt, the product was immersed in a sufficient quantity of water to completely cover it, stirred for several minutes and filtered. The filtrate was retained, and dried, but no solid crystallized from the solution, indicating that no soluble acid was still present on the silica. A similar sample of 40% loading was prepared analogously. Also, bulk (unsupported) $Cs_{2.5}H_{0.5}PW_{12}O_{40}$ was prepared as described in the prior art by adding a cesium carbonate solution to a solution of the 12-tungstophosphoric acid and forming a fine water-insoluble precipitate. FIG. 2 shows the X-ray diffraction spectra of the conventional bulk Cs-acid salt and the 40% Cs-acid salt supported on silica. From these spectra, it is clear that this technique produces the cesium acid salt supported on the silica powder.

Example 3

40% $Cs_{2.5}H_{0.5}PW_{12}O_{40}/SiO_2$ by sequential impregnation (1/16"-diameter silica extrudates 260 $m^2/g$.

Catalyst Preparation: 40 grams of 1/16" silica extrudates measuring between 1/8 and 3/8" long were precalcined at 600° C. overnight. The silica had a surface area of 260 $m^2/g$. 3.39 grams of cesium carbonate was dissolved in 44 cc $H_2O$ and this solution was impregnated to the point of incipient wetness. The sample was then dried at 120° C., and calcined at 300° C. for 3 hours. A solution of 24.9 grams of $H_3PW_{12}O_{40} \cdot 6H_2O$, which was prepared from a commercial supply (Allan Chemicals) by drying at 120° C. was then dissolved in 44 cc of $H_2O$ and impregnated by incipient wetness onto the Cs-impregnated extrudate, dried overnight at 120° C. and calcined at 300° C. for three hours. The X-ray diffraction spectra of the ground extrudate looked similar to the one described in example two for the powder silica catalyst confirming that the Cs-acid salt was formed supported on the extrudate.

Back-scattered electron images (see FIG. 3) of extrudates that had been snapped perpendicular to their longitudinal axis were collected and showed that typically the Cs-acid salt was located in an internal ring in an eggwhite configuration with more than 50% of the acid salt being present in the ring. The typical ring diameter was on the order of 10 microns. Therefore it is seen that, the acid-salt had been successfully deposited into the interior of the large silica particle.

Example 4

A series of strong acid catalysts were compared with the cesium acid salt of 12-tungstophosphoric acid for the alkylation of mesitylene with cyclohexene. 0.5 gm of catalyst freshly calcined at the temperatures indicated to remove adsorbed water were loaded with 150 cc of trimethylbenzene into a 250 cc autoclave, pressurized to 15 psi $N_2$ and heated to 100° C. while stirring at 600 rpm. When the temperature equilibrates at 100° C., the stirring is stopped, the autoclave depressurized, and 8 cc of cyclohexene are injected by syringe into the autoclave. Mixing is resumed and the autoclave repressurized to 15 psi. Samples are periodically withdrawn at 1, 15, 30, 45, 60, 90, and 120 minute intervals. The one minute sample is used to calculate feed composition. All samples are analyzed by gc. Table 1 shows the conversions measured after two hours of reaction.

TABLE 1

| Catalyst | wt. catalyst (grams) | Calcination Temperature (°C.) | % cyclohexene Conversion (2 hr) |
|---|---|---|---|
| amorphous $SiO_2$—$Al_2O_3$ (75 wt % $SiO_2$; 25% $Al_2O_3$) | 0.5 | 500 | 0.8 |
| H-mordenite | 0.5 | 450 | 1.2 |
| bulk 12-tungstophosphoric acid $H_3PW_{12}O_{40} \cdot 6H_2O$ (HPW) | 0.5 | 120 | 1.1 |
| bulk ammonium acid-salt of 12-tungstophosphoric acid $(NH_4)_{3-x}H_xPW_{12}O_{40}$ | 0.5 | 300 | 28 |
| $ZrO_2/SO_4$ | 0.5 | 575 | 1.2 |

TABLE 1-continued

| Catalyst | wt. catalyst (grams) | Calcination Temperature (°C.) | % cyclohexene Conversion (2 hr) |
|---|---|---|---|
| 24% $HPW/SiO_2$ | 2.06 equivalent to (0.5 gm HPW) | 300 | 98 |
| $Cs_{2.5}H_5PW_{12}O_{40}$ (bulk) | 0.5 | 300 | 90 |

Tables 1 and 2 show that both the Cs-acid salt and 12-tungstophosphoric acid supported on silica were the most active catalysts for mesitylene alkylation. For alkylation reactions that contain a polar reactant such as phenol, the Cs acid salt is the preferred catalyst because of its lower solubility.

Example 5

Four catalysts were compared for the alkylation of mesitylene with cyclohexene. All catalysts were calcined at 300° C. prior to use. Catalyst C and D are the subject of this invention and described in Example 3. The reaction was carried out as described in Example 4.

TABLE 2

| Catalyst | Wt. Catalyst (grams) | % Cyclohexene Conversion (2 Hr) |
|---|---|---|
| A 24% $HPW/SiO_2$ | 2.06 (equivalent to 0.5 gm HPW) | 98 |
| B $Cs_{2.5}H_5PW_{12}O_{40}$ (bulk) | 0.5 | 90 |
| C 40% $Cs_{2.5}H_5PW_{12}O_{40}/SiO_2$ powder (270 $m^2/g$); ≅0.1–0.2 mm particle size | 1.25 (equivalent to 0.5 gm $Cs_{2.5}H_5PW_{12}O_{40}$) | 91 |
| D 40% $Cs_{2.5}H_5PW_{12}O_{40}/SiO_2$ extrudates (1/16" diameter; 280 $m^2/g$ | 1.25 (equivalent to 0.5 gm $Cs_{2.5}H_5PW_{12}O_{40}$) | 38 |

Table 2 shows that the supported cesium acid salt made by the technique described herein is effective in mesitylene alkylation. The Cs-acid salt on the silica powder has the same activity as the bulk Cs acid salt per gram of acid salt. The activity of the extrudate is slightly lower due to diffusional restrictions of the reactants entering into the large particle extrudate.

Example 6

9 grams of the catalyst of Example 1 consisting of 24% $(NH_4)_{3-x}H_xPW_{12}O_{40}/SiO_2$ was mixed with 72 gm dichlorobenzene and 28 gm of phenol. The mixture was heated to 170° C. and held for 5 hours at which time the liquid was extracted and tested for tungsten content. 5.4 gm of a comparative sample of 12.2% $HPW/SiO_2$ was mixed with 14.2 gm phenol and 39.2 gm of dichlorobenzene and heated under similar conditions and analyzed. The results are shown below:

| Catalyst | Solubility in phenol/DCB at 170° C. |
|---|---|
| 12% $HPW/SiO_2$ | 3100 ppm |
| 24% $(NH_4)_{3-x}H_xPW_{12}O_{40}$ | 194 pm |

Consequently the supported ammonium phosphotungstate salt is appreciably less soluble than the supported acid. Similar results are found with the supported Cs-acid salt.

Example 7

Reaction test: 50 grams of an ethylene-butene copolymer containing about 46.9% ethylene with a vinylidene double bond content of 47% and an average molecular weight of 3670 were mixed with 28 grams of phenol, 25 grams of o-dichlorobenzene as solvent, and 25 grams of the 8 wt % $(NH4)_{3-x}H_xPW_{12}O_{40}/SiO_2$ (Davison 62)-catalyst described above. The reactants and catalyst were charged into a four necked round bottomed flask equipped with an air stirrer, thermometer, condenser and nitrogen blanket and the reaction was carried out at 175° C. for a total time of 6 hours. After two hours a sample was withdrawn, filtered and stripped and analyzed for 58.1% alkylated phenol and after six hours the sample showed 68.6% conversion to alkylated phenol.

Example 8

Same catalyst as Example 3.

17583-130: 40 grams of the polymer of Example 7were charged into a reaction flask and mixed with 23 grams of phenol and 50 grams of the Example 3 catalyst (freshly calcined at 300° C.,1 h)—no solvent was added. The reaction mixture was then heated to 175° C. for 6 hours under mixing. The samples analyzed for: 64.3% conversion to alkylate at 2 hours and 71.8 at 6 hours.

Example 9

Reaction Test: 50 grams of an ethylene-butene copolymer containing about 46.9% ethylene, 39% vinylidene double bonds and an average molecular weight of 3670 were mixed with 15 grams of phenol, 25 grams of n-decane as solvent and 34 grams of the 30% $Cs_{2.5}H_{0.5}PW_{12}O_{40}/SiO_2$ catalyst of Example 2. The reaction mixture was then heated to 150° C. while stirring under a nitrogen blanket for a period of 6 hours. The two hour sample analyzed for 64.9% alkylated phenol and the six hours sample showed 75.8% conversion to the alkylate.

What is claimed is:

1. An aromatic alkylation process comprising contacting at aromatic alkylation conditions a catalyst composition comprising a heteropoly compound selected from the group consisting of heteropoly salts and heteropolyacid salts deposited in the interior of a porous support selected from the group consisting of silica, titania, and zirconia, wherein said salt of said heteropoly salt and said heteropolyacid salt is selected from the group consisting of ammonium, cesium, potassium, and rubidium salts and mixtures thereof, and wherein said heteropoly salt and said heteropolyacid salt are formed with a heteropolyacid selected from the group consisting of 12-tungstophosphoric, 12-tungstosilicic, 12-molybdophosphoric, and 12-molybdosilicic acid with a feed comprising an aromatic compound selected from the group consisting of benzene, toluene, and phenol with an olefin selected from the group consisting of $C_2$ to olefins having a molecular weight up to 5000 inclusive.

2. A process according to claim 1 wherein said heteropoly salts and said heteropolyacid salts are deposited on the interior of a support in an egg white configuration.

* * * * *